United States Patent
Tian et al.

(10) Patent No.: US 10,668,021 B2
(45) Date of Patent: Jun. 2, 2020

(54) METFORMIN HYDROCHLORIDE OSMOTIC PUMP TABLET AND PREPARATION METHOD THEREFOR

(71) Applicant: ELITE PHARMA TECHNOLOGY (SHANGHAI) CO., LTD., Shanghai (CN)

(72) Inventors: Wu Tian, Shanghai (CN); Qing Tian, Jiangsu (CN); Jianping Jiang, Shanghai (CN)

(73) Assignee: ELITE PHARMA TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/084,416

(22) PCT Filed: Jul. 27, 2016

(86) PCT No.: PCT/CN2016/091933
§ 371 (c)(1),
(2) Date: Sep. 12, 2018

(87) PCT Pub. No.: WO2017/156953
PCT Pub. Date: Sep. 21, 2017

(65) Prior Publication Data
US 2019/0076364 A1    Mar. 14, 2019

(30) Foreign Application Priority Data
Mar. 17, 2016  (CN) .......................... 2016 1 0153028

(51) Int. Cl.
*A61K 9/20*        (2006.01)
*A61K 31/155*      (2006.01)
(Continued)

(52) U.S. Cl.
CPC .......... *A61K 9/2072* (2013.01); *A61K 9/0004* (2013.01); *A61K 9/2018* (2013.01);
(Continued)

(58) Field of Classification Search
CPC .. A61K 9/0004; A61K 9/2031; A61K 9/2054; A61K 9/2027; A61K 9/2866; A61K 9/2072; A61K 9/2018; A61K 31/155
See application file for complete search history.

(56) References Cited

U.S. PATENT DOCUMENTS

2010/0316708 A1* 12/2010 Kositprapa .......... A61K 9/0004
424/465
2012/0093878 A1* 4/2012 Singh .................... A61K 9/209
424/400

FOREIGN PATENT DOCUMENTS

CN    101904829 A    12/2010
CN    102525991 A     7/2012
(Continued)

OTHER PUBLICATIONS

2009 Tableting Toolings paper by the Tablet Press Company.*
(Continued)

*Primary Examiner* — Blessing M Fubara
(74) *Attorney, Agent, or Firm* — Norton Rose Fulbright US LLP; James R. Crawford

(57) ABSTRACT

Provided are a metformin hydrochloride osmotic pump tablet and a preparation method therefor. According to the preparation method, a hetero-type stamping-prepared metformin hydrochloride tablet core is used, and a controlled-release coating is wrapped outside the stamped metformin hydrochloride tablet core, such that the metformin hydrochloride osmotic pump tablet is prepared.

16 Claims, 3 Drawing Sheets

(51) Int. Cl.
*A61K 9/00* (2006.01)
*A61K 9/28* (2006.01)

(52) U.S. Cl.
CPC .......... *A61K 9/2027* (2013.01); *A61K 9/2031* (2013.01); *A61K 9/2054* (2013.01); *A61K 9/2866* (2013.01); *A61K 31/155* (2013.01)

(56) References Cited

FOREIGN PATENT DOCUMENTS

| CN | 103070864 A | 5/2013 |
|---|---|---|
| CN | 103961351 A | 8/2014 |
| CN | 104337811 A | 2/2015 |

OTHER PUBLICATIONS

V. Buhler "Polyvinylpyrrolidone Excipients for Pharmaceuticals" Chapter 2. Soluble Polyvinylpyrrodone (Povidone), Dec. 17, 2006 pp. 5-124.*

* cited by examiner

METFORMIN HYDROCHLORIDE OSMOTIC PUMP TABLET AND PREPARATION METHOD THEREFOR

This application is a § 371 of International Application No. PCT/CN2016/091933 filed Jul. 27, 2016, and claims priority from Chinese Patent Application No. 201610153028.8 filed on Mar. 17, 2016. The entire contents of these applications are incorporated herein by reference in their entirety.

TECHNICAL FIELD

The present disclosure belongs to the field of pharmaceutical preparations, and relates to a metformin hydrochloride osmotic pump tablet and a preparation method thereof, in particular to a metformin hydrochloride osmotic pump tablet prepared by using a special-shaped punch and a preparation method thereof.

BACKGROUND

With the development of pharmaceutical science, therapeutic advantages of oral sustained-release preparations over ordinary immediate-release preparations have been recognized. The sustained-release preparation has longer drug release time, and more stable drug release, so that the fluctuation in plasma drug concentration is reduced in patients, which can reduce the times of medication and improve therapeutic effects, while also reduce the occurrence of side effects. Therefore, in the research & development of pharmaceutical preparations, more and more drugs are designed as sustained-release preparations.

In practical applications, in order to achieve the purpose of controlling drug release, it is often necessary to use more adjuvant materials that control drug release. However, the use of a large amount of adjuvant materials inevitably leads to a larger weight and volume of the final preparations, thereby causing difficulties for patients to swallow.

According to statistical data from the Food and Drug Administration, 16 million people in the United States have difficulties in swallowing. Among them, 8% have experienced cases where the preparation is too large to be swallowed and the medication is not strictly taken as prescribed, even 4% give up the treatment with a certain preparation as it is unable to be swallowed. Therefore, it is a subject closely related to therapeutic effects of a drug in terms of controlling the weight and volume of a pharmaceutical preparation to make it easy for patients to swallow.

For example, metformin hydrochloride framework sustained-released tablets have two commonly used specifications of 500 mg and 1000 mg. A framework controlled-release mechanism is used by the metformin hydrochloride sustained-released tablets sold at the pharmaceutical market in China to control drug release, and a framework sustained-released tablet with a specification of 500 mg has a weight of more than 1 gram (about 1.1 grams). For convenience of administration by patient, tablets are made into capsule-shaped ones to reduce their cross-sectional area through the esophagus when swallowing. If a framework sustained-released tablet with a specification of 1000 mg is produced by way of framework sustained-release method, the weight will reach more than 2 g. Even if the capsule-shaped design is used, the volume is too large, which will make it difficult for patient to swallow. Therefore, the metformin hydrochloride sustained-released tablets sold at the pharmaceutical market in China only have a maximum specification of 500 mg, rather than a specification of 1000 mg.

Among metformin hydrochloride controlled-release preparations sold at the American market, there are metformin hydrochloride osmotic pump tablets with a specification of 1000 mg (trade name: FORTMET) manufactured by Andrx Labs. Since in an osmotic pump preparation, a coating film is used as controlled-release means, a controlled-release effect can be achieved with less adjuvant materials, so that the total weight of such preparation is only about 1.2 grams, which is much lower than the weight of the framework sustained-released tablet (more than 2 grams). A circular-shaped punch is adopted for the FORTMET osmotic pump tablet to press a tablet core, and the punch used for preparing the osmotic pump tablet is a circular-shaped punch for the reason that the tablet core pressed via a circular-shaped punch is isotropic, the tumbling of the tablet core in the coating pan is random in the process of coating, and the probability of receiving the coating liquid in each direction is the same, therefore, the coating film on the entire surface of the tablet is relatively uniform, so that the coating film has good integrity and is not easily broken to cause burst release. However, a circular-shaped punch with a diameter of 13-14 mm is adopted for the FORTMET osmotic pump tablet to press the tablet core, although the weight of the tablet is significantly lower than that of the framework sustained-released tablet, the cross-sectional area is still large and it is still inconvenient to be swallowed.

SUMMARY

In view that a metformin hydrochloride controlled-release preparation existing in the related technics has a large cross-sectional area and is inconvenient to be swallowed, the present disclosure provides a metformin hydrochloride osmotic pump tablet and a preparation method thereof. According to the preparation method of the present disclosure, a metformin hydrochloride tablet core is pressed by using a special-shaped punch, and the pressed metformin hydrochloride tablet core is wrapped with a controlled-release coating film, such that the metformin hydrochloride osmotic pump tablet is prepared. The metformin hydrochloride osmotic pump tablet prepared by the present disclosure has a small tablet weight, and a metformin hydrochloride osmotic pump tablet with a specification of 1000 mg has a tablet weight of only about 1.2 g. Since the metformin hydrochloride tablet core is pressed by using a special-shaped punch, the cross-sectional area of the metformin hydrochloride osmotic pump tablet is reduced by more than 40% compared to that of the circular-shaped tablet with the same weight, thereby the swallowability of the tablet is greatly improved.

To achieve this object, the present disclosure adopts the following technical solutions:

In a first aspect, the present disclosure provides a preparation method for a metformin hydrochloride osmotic pump tablet. The preparation method comprises: using a special-shaped punch to press a metformin hydrochloride tablet core, and wrapping the pressed metformin hydrochloride tablet core with a controlled-release coating film to prepare the metformin hydrochloride osmotic pump tablet.

The followings are preferred technical solutions of the present disclosure, but are not interpreted as limitations to the technical solutions provided by the present disclosure.

The technical objects and beneficial effects of the present disclosure can be better achieved and realized by the following technical solutions.

As a preferred technical solution of the present disclosure, the method comprises the following steps:

(1) formulating a binder solution, mixing the metformin hydrochloride, a tablet core adjuvant material and the binder solution for granulation, and then drying and straightening granulating;

(2) pressing granules obtained by straightening granulation via a special-shaped punch into a metformin hydrochloride tablet core;

(3) wrapping the prepared metformin hydrochloride tablet core with a controlled-release coating film to obtain a metformin hydrochloride osmotic pump tablet.

As a preferred technical solution of the present disclosure, the special-shaped punch is a capsule-shaped punch or an ellipse-shaped punch.

Preferably, when a special-shaped punch is used, the ratio of the long diameter to the short diameter of the metformin hydrochloride tablet core is controlled to be from 1.2 to 4, for example 1.2, 1.3, 1.5, 1.8, 2.0, 2.2, 2.5, 2.8, 3.0, 3.2, 3.5, 3.8, 3.9 or 4, etc. However, it is not limited to the numerical values listed, and other values in the range listed can also be used, and further preferably from 1.5 to 3, and most preferably the ratio of the long diameter to the short diameter is from 1.8 to 2.7.

In the present disclosure, use of a non-circular (e.g., capsule-shaped or ellipse-shaped) tablet core pressed via a special-shaped punch to prepare a metformin hydrochloride osmotic pump tablet has a problem that unlike a circular tablet core that is isotropic, the motion state of a non-circular (e.g., capsule-shaped or ellipse-shaped) tablet core in the coating pan is more like a rolling with the long diameter as the axis in the coating pan, therefore the non-circular (e.g., capsule-shaped or ellipse-shaped) tablet core is less likely to receive the coating liquid at both ends than the middle part. Such type of motion results in the controlled-release coating film of the non-circular (e.g., capsule-shaped or ellipse-shaped) tablet core may not be uniform enough, especially the controlled-release coating film at both ends of the tablet core is likely to be thinner than the controlled-release coating film at the middle part. Therefore, it may cause the osmotic pump tablet to rupture during the release process, resulting in the risk of the burst release of drugs.

The above problem is more obvious especially when the ratio of the long diameter to the short diameter of the non-circular (e.g., capsule-shaped or ellipse-shaped) tablet core is larger, because if it is larger, the tablet core is more slender, the probability of receiving the coating liquid at both ends of the tablet core is lower, and the possibility of producing uneven coating film is higher. The present disclosure has been repeatedly verified by experiments and concludes that when the ratio of the long diameter to the short diameter of the non-circular (e.g., capsule-shaped or ellipse-shaped) tablet core is greater than 4, the controlled-release coating film at both ends of the tablet core is significantly thinner than that at the middle part of the tablet core. In order to make the controlled-release coating film not damaged, it is necessary to greatly increase the thickness of the controlled release coating film (for example, 20 wt % weight gain of the coating film), however, the release rate of the tablet under such condition will be significantly affected. Therefore, when designing the osmotic pump tablet into a special-shaped tablet, the ratio of the long diameter to the short diameter of the metformin hydrochloride tablet core should be controlled to be from 1.2 to 4, when the ratio is controlled to be 1.8 to 2.7, the most excellent effect can be achieved.

Preferably, a drug release channel is produced on the controlled-release coating film wrapping the metformin hydrochloride osmotic pump tablet. In the present disclosure, the drug release channel may be produced on the controlled-release coating film wrapping the metformin hydrochloride osmotic pump tablet, or the drug release channel may not be produced. When the drug release channel is not produced, the drug may be released through a channel remained after the dissolution of the porogen.

Preferably, the number of the drug release channel is 1 or more, for example 1, 2, 3, 4 or in 5 and more, it is not limited to the numerical values listed above.

As a preferred technical solution of the present disclosure, after the metformin hydrochloride tablet core is wrapped with a controlled-release coating film, the weight gain of the controlled-release coating film is 2 wt % or more, for example 2 wt %, 2.1 wt %, 2.3 wt %, 2.5 wt %, 3 wt %, 4 wt %, 5 wt %, 6 wt %, 7 wt %, 8 wt %, 9 wt %, 10 wt %, 12 wt %, 15 wt %, 18 wt % or 20 wt %, etc., based on the weight of the tablet core. However, it is not limited to the numerical values listed above, and further preferably from 2.5 wt % to 10 wt %, particularly preferably from 3 wt % to 8 wt %.

In the present disclosure, the weight gain of the controlled-release coating film also affects its integrity. If the controlled-release coating film is too thin, the possibility that both ends of the non-circular (e.g., capsule-shaped or ellipse-shaped) tablet core cannot be wrapped with the controlled-release coating film is higher, thus the weight gain of the controlled-release coating film should be at least 2 wt % or more of the weight of the tablet core.

As a preferred technical solution of the present disclosure, formulating a binder solution in step (1) is performed by way of mixing a binder with a solvent to prepare a binder solution.

Preferably, the binder is any one or a combination of at least two of povidone, hypromellose or hydroxypropylcellulose. Typical but non-limiting examples of such combinations are: a combination of povidone and hypromellose, a combination of hypromellose and hydroxypropylcellulose, and a combination of povidone, hypromellose and hydroxypropylcellulose, and the like.

Preferably, the solvent is ethanol having a purity of 95 wt % and/or water.

Preferably, when the binder is povidone and the solvent is ethanol having a purity of 95 wt %, the mass ratio of povidone to ethanol having a purity of 95 wt % is (10-15): (90-85), for example 10:90, 11:89, 12:88, 13:87, 14:86 or 15:85, etc. However, it is not limited to the numerical values listed, and other values in the range listed can also be used, and further preferably 15:85.

Preferably, when the binder is hypromellose and the solvent is water, the mass ratio of hypromellose to water is (10-15):(290-285), for example 10:290, 11:289, 12:288, 13:287, 14:286 or 15:285, etc. However, it is not limited to the numerical values listed, and other values in the range listed can also be used, and further preferably 15:285.

As a preferred technical solution of the present disclosure, the tablet core adjuvant material in step (1) comprises sodium lauryl sulfate and a filler.

Preferably, the filler is any one or a combination of at least two of polysorbate, sorbitol or mannitol. Typical but non-limiting examples of such combinations are: a combination of polysorbate and sorbitol, a combination of sorbitol and mannitol, a combination of polysorbate and mannitol, and a combination of polysorbate, sorbitol and mannitol, and the like.

Preferably, in step (1), the binder solution, metformin hydrochloride, sodium lauryl sulfate and a filler are mixed in the following parts by weight:

| | |
|---|---:|
| metformin hydrochloride | 1000 parts |
| sodium lauryl sulfate | 5-70 parts |
| filler | 100-155 parts |
| the binder solution | 95-300 parts; | wherein, the parts by weight of the sodium lauryl sulfate can be 5 parts, 10 parts, 15 parts, 20 parts, 25 parts, 30 parts, 35 parts, 40 parts, 45 parts, 50 parts, 55 parts, 60 parts, 65 parts or 70 parts, etc., however, it is not limited to the numerical values listed, and other values in the range listed can also be used; the parts by weight of the filler can be 100 parts, 105 parts, 110 parts, 115 parts, 120 parts, 125 parts, 130 parts, 135 parts, 140 parts, 145 parts, 150 parts or 155 parts, etc., however, it is not limited to the numerical values listed, and other values in the range listed can also be used; and the parts by weight of the binder solution can be 95 parts, 100 parts, 120 parts, 150 parts, 170 parts, 200 parts, 230 parts, 250 parts, 270 parts or 300 parts, etc., however, it is not limited to the numerical values listed, and other values in the range listed can also be used.

Preferably, in step (1), the binder solution, metformin hydrochloride, sodium lauryl sulfate and polysorbate are mixed in the following parts by weight:

| | |
|---|---:|
| metformin hydrochloride | 1000 parts |
| sodium lauryl sulfate | 5 parts |
| polysorbate | 150 parts |
| the binder solution | 100 parts. |

Preferably, in step (1), the binder solution, metformin hydrochloride, sodium lauryl sulfate and mannitol are mixed in the following parts by weight:

| | |
|---|---:|
| metformin hydrochloride | 1000 parts |
| sodium lauryl sulfate | 25 parts |
| mannitol | 100 parts |
| the binder solution | 300 parts. |

As a preferred technical solution of the present disclosure, a lubricant is added to the straightening granulation process in step (1).

Preferably, the lubricant is magnesium stearate.

Preferably, the lubricant is added in an amount from 0.5% to 1% of the mass of metformin hydrochloride, for example 0.5%, 0.6%, 0.7%, 0.8%, 0.9% or 1%, etc., however, it is not limited to the numerical values listed, and other values in the range listed can also be used.

As a preferred technical solution of the present disclosure, the coating liquid used in the process of wrapping with the controlled-release coating film comprises a controlled-release material and a porogen. In the present disclosure, the coating liquid can also be added other active ingredients in addition to a controlled-release material and a porogen.

Preferably, the controlled-release material is cellulose acetate and/or ethyl cellulose.

Preferably, the porogen is polyethylene glycol.

Preferably, the coating liquid is mainly composed of the following components in parts by weight:

| | |
|---|---:|
| the controlled-release material | 20-30 parts |
| porogen | 10-20 parts |
| solvent | 750-760 parts; | wherein, the parts by weight of cellulose acetate and/or ethyl cellulose can be 20 parts, 22 parts, 24 parts, 26 parts, 28 parts or 30 parts, etc., however, it is not limited to the numerical values listed, and other values in the range listed can also be used; the parts by weight of polyethylene glycol can be 10 parts, 12 parts, 14 parts, 16 parts, 18 parts or 20 parts, etc., however, it is not limited to the numerical values listed, and other values in the range listed can also be used; and the parts by weight of the solvent can be 750 parts, 752 parts, 754 parts, 756 parts, 758 parts or 760 parts, etc., however, it is not limited to the numerical values listed, and other values in the range listed can also be used.

Preferably, the solvent is any one or a combination of at least two of ethanol, acetone or water.

In a second aspect, the present disclosure provides a metformin hydrochloride osmotic pump tablet prepared by the preparation method as described above, comprising a metformin hydrochloride tablet core and a controlled-release coating film wrapping the metformin hydrochloride tablet core, wherein the ratio of the long diameter to the short diameter of the metformin hydrochloride osmotic pump tablet is from 1.2 to 4, for example 1.2, 1.3, 1.5, 1.8, 2.0, 2.2, 2.5, 2.8, 3.0, 3.2, 3.5, 3.8, 3.9 or 4, etc., however, it is not limited to the numerical values listed, and other values in the range listed can also be used, and further preferably from 1.5 to 3, particularly preferably from 1.8 to 2.7.

As a preferred technical solution of the present disclosure, the metformin hydrochloride osmotic pump tablet is non-circular.

Preferably, the metformin hydrochloride osmotic pump tablet is capsule-shaped.

Preferably, the metformin hydrochloride osmotic pump tablet is ellipse-shaped.

Compared with the related technics, the present disclosure has the following beneficial effects:

The preparation method of the present disclosure comprises: using a special-shaped punch-pressed metformin hydrochloride tablet core, and then wrapping the pressed metformin hydrochloride tablet core with a controlled-release coating film, such that a metformin hydrochloride osmotic pump tablet is prepared. The metformin hydrochloride osmotic pump tablet prepared by the present disclosure has a small tablet weight, and a metformin hydrochloride osmotic pump tablet with a specification of 1000 mg has a tablet weight of only about 1.2 g; moreover, on the premise that the obtained metformin hydrochloride osmotic pump tablet reaches the same drug controlled-release effect as that of the related technics, the cross-sectional area of the osmotic pump tablet is significantly reduced, which is reduced even more than 50%, compared to that of a traditional sustained-release tablet with the same weight, so that the resulting osmotic pump tablets are easier to be swallowed, greatly improving the compliance of patients.

DETAILED DESCRIPTION

Figure 1:
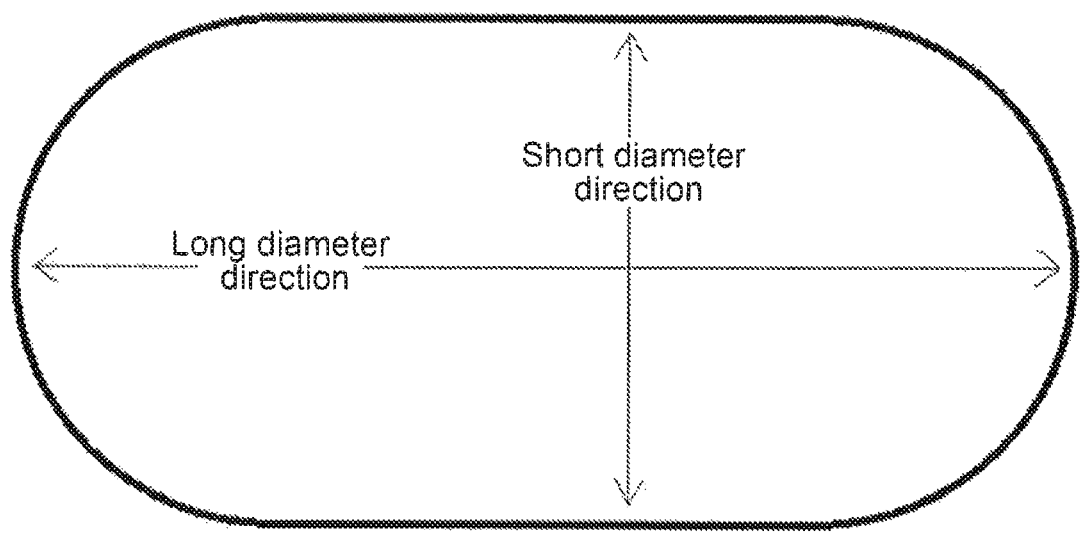
FIG. 1 is a schematic diagram showing the shape of the metformin hydrochloride osmotic pump tablet of the present disclosure.

In order to better illustrate the present disclosure, and easily understand the technical solution of the present disclosure, the present disclosure will be further described in detail below. However, the following examples are merely simple examples of the present disclosure, which do not represent or limit the claimed scope of the present disclosure that is only defined by the claims.

The specific example part of the present disclosure provides a metformin hydrochloride osmotic pump tablet and a preparation method thereof, and the preparation method comprises the following steps:

(1) formulating a binder solution, mixing metformin hydrochloride, a tablet core adjuvant material and the binder solution for granulation, and then drying and straightening granulating;

(2) pressing granules obtained by straightening granulation via a special-shaped punch into a metformin hydrochloride tablet core;

(3) wrapping the prepared metformin hydrochloride tablet core with a controlled-release coating film to obtain the metformin hydrochloride osmotic pump tablet.

Example 1

The proportion of each raw material used in this example is as shown in Table

TABLE 1

Table of proportions of raw materials

| | Components | Gram/batch |
|---|---|---|
| Drug-containing granule | Metformin hydrochloride | 1000 |
| | Sodium lauryl sulfate | 5 |
| | Polysorbate | 150 |
| The binder solution | Povidone K30 | 15 |
| | 95% Ethanol | 85 |
| Added adjuvant materials | Magnesium stearate | 5 |
| Coating liquid | Cellulose acetate | 30 |
| | Polyethylene glycol 3350 | 10 |
| | Acetone | 720 |
| | Water | 40 |

(1) Povidone K30 and 95 wt % of ethanol were mixed according to the proportions of raw materials to form a binder solution;

(2) Metformin hydrochloride, sodium lauryl sulfate and polysorbate were added to a wet type granulator according to the proportions of raw materials, and the mixture was mixed for 3 minutes under the condition of stirring paddle rotation speed of 75 r/min and cutter rotation speed of 500 r/min; then the rotation speed of the stirring paddle was unchanged, while the rotation speed of the cutter was increased to 1000 r/min, and then the binder solution was slowly added to the wet type granulator within about 1 minute to obtain wet granules;

(3) The obtained wet granules were wet straightening granulated by a Quadro Comil straightening granulator, and then dried by a fluidized bed. During the drying process, the temperature of the inlet air was set at 50° C., the frequency of the air blower was set at 20 Hz, and the weight loss on drying was measured every 5 minutes until the value of the weight loss on drying was less than 1 wt %, and then straightening granulated by a Quadro Comil straightening granulator (0.05 in. sieve diameter);

(4) The granules obtained by straightening granulation were mixed with magnesium stearate at a rotation speed of 25 r/min for 10 minutes, and then pressed into a tablet core containing 1000 mg of metformin hydrochloride per tablet with a capsule-shaped punch of 19×7.9 mm;

(5) Polyethylene glycol 3350 was dissolved in water according to the original proportion to obtain an aqueous polyethylene glycol 3350 solution, and a formulation amount of cellulose acetate was dissolved in acetone to obtain a solution of cellulose acetate in acetone, and then the aqueous polyethylene glycol 3350 solution was added to the solution of cellulose acetate in acetone to obtain a coating liquid;

(6) a metformin hydrochloride tablet core was coated with the coating liquid prepared in step (5), wherein the coated tablet bed had a temperature of 40° C., an atomization pressure of 0.6 Mpa, a blow-flattening pressure of 0.2 Mpa, and a flow rate of the coating liquid of 40-45 g/min. When the weight gain of the coating reached about 5%, the coating was stopped, dried in an oven at 40° C. for 24 hours, and then 0.6 mm of drug release channels were punched on both sides of the tablet core to obtain a metformin hydrochloride osmotic pump tablet.

The metformin hydrochloride osmotic pump tablet with a specification of 1000 mg prepared in this example had a tablet weight of only about 1.2 g, and a ratio of the long diameter to the short diameter of 2.4, and the cross-sectional area thereof can be reduced by 50% compared with that of the conventional sustained-release tablet (pressed by use of a circular-shaped punch), and the sustained-release curve thereof was as shown in FIG. 1. It can be seen that the metformin hydrochloride osmotic pump tablet can reach the same drug controlled-release effect in the phosphate buffer solution of pH 6.8 at 50 r/min in the paddle method as that in the related technics.

Example 2

The proportion of each raw material used in this example is as shown in Table 2:

TABLE 2

Table of proportions of raw materials

| | Components | Gram/batch |
|---|---|---|
| Drug-containing granule | Metformin hydrochloride | 1000 |
| | Sodium lauryl sulfate | 25 |
| | Mannitol | 100 |
| The binder solution | Hypromellose E3 | 15 |
| | Water | 285 |
| Added adjuvant materials | Magnesium stearate | 5 |
| Coating liquid | Ethyl cellulose | 20 |
| | Polyethylene glycol 3350 | 20 |
| | Absolute ethanol | 720 |
| | Water | 40 |

(1) Hypromellose E3 was mixed with water according to the proportions of raw materials to form a binder solution;

(2) Metformin hydrochloride, sodium lauryl sulfate and mannitol were added to a fluidized bed granulator according to the proportions of raw materials, then top-spray granulated at the temperature of the inlet air of 50° C., the frequency of the air blower of 20 Hz, and the atomization pressure of 0.4 Mpa. Then, the binder solution was added, dried under the same conditions, the weight loss on drying was measured every 5 minutes until the value of the weight loss on drying was less than 1%, and then straightening granulated by a Quadro Comil straightening granulator (0.05 in. sieve diameter);

(3) The granules obtained by straightening granulation were mixed with magnesium stearate at a rotation speed of 25 r/min for 10 minutes, and then pressed into a tablet core containing 1000 mg of metformin hydrochloride per tablet with a capsule-shaped punch of 19×7.9 mm;

(4) Polyethylene glycol 3350 was dissolved in water according to the original proportion to obtain an aqueous polyethylene glycol 3350 solution, and a formulation amount of ethyl cellulose was dissolved in absolute ethanol to obtain a solution of ethyl cellulose in ethanol, and then the aqueous polyethylene glycol 3350 solution was added to the solution of ethyl cellulose in ethanol to obtain a coating liquid;

(6) a metformin hydrochloride tablet core was coated with the coating liquid prepared in step (4), wherein the coated tablet bed had a temperature of 40° C., an atomization pressure of 0.6 Mpa, a blow-flattening pressure of 0.2 Mpa, and a flow rate of the coating liquid of 40-45 g/min. When the weight gain of the coating reached about 5%, the coating was stopped, dried in an oven at 40° C. for 24 hours, and then 0.6 mm of drug release channels were punched on both sides of the tablet core to obtain a metformin hydrochloride osmotic pump tablet.

Figure 2:
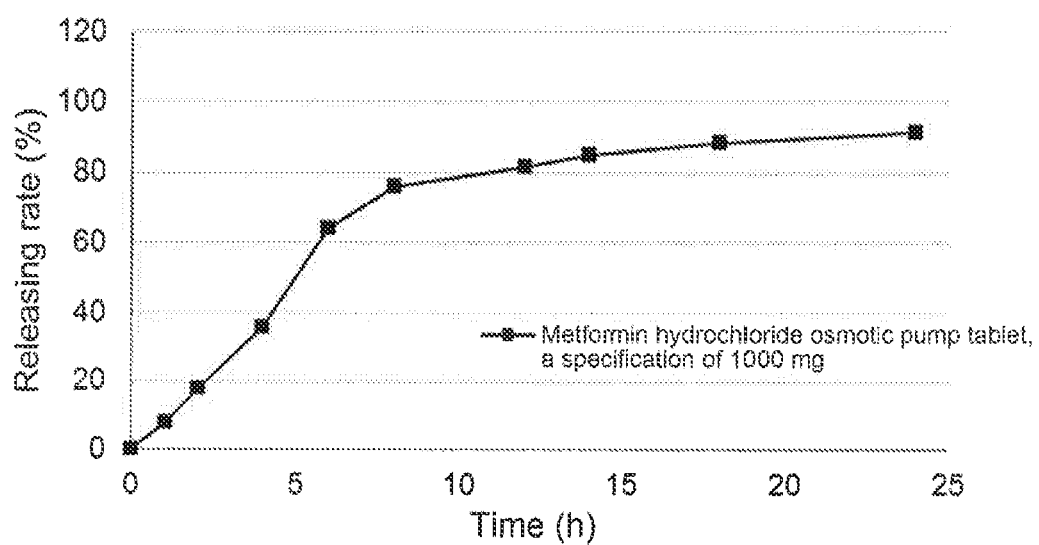
FIG. 2 is a release curve of a metformin hydrochloride osmotic pump tablet prepared in Example 1 of the present disclosure.
Figure 3:
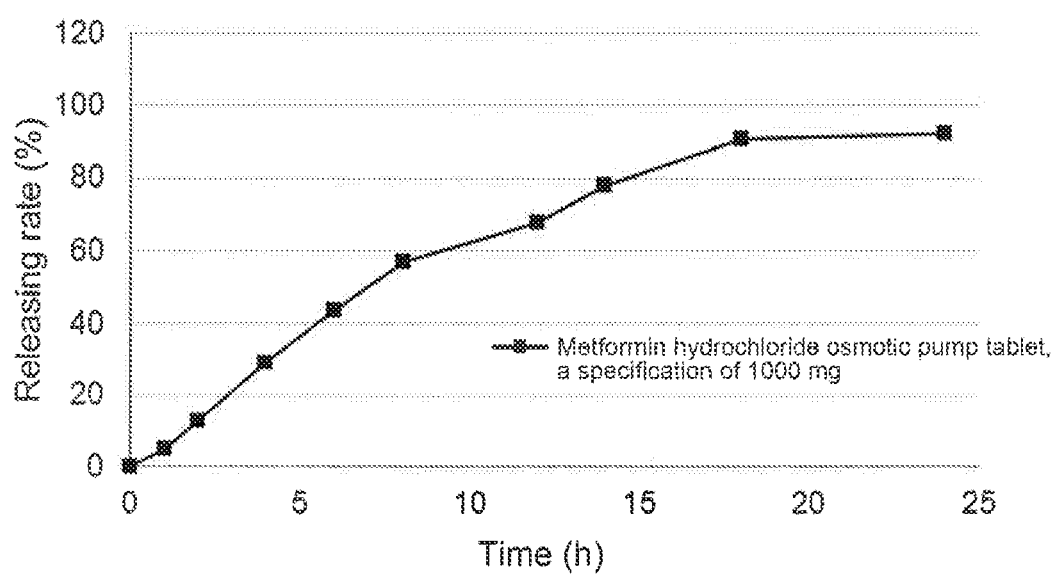
FIG. 3 is a release curve of a metformin hydrochloride osmotic pump tablet prepared in Example 1 of the present disclosure.

The metformin hydrochloride osmotic pump tablet with a specification of 1000 mg prepared in this example had a tablet weight of only about 1.2 g, and a ratio of the long diameter to the short diameter of 2.4, and the cross-sectional area thereof can be reduced by 50% compared with that of the conventional sustained-release tablet (pressed by use of a circular-shaped punch), and the sustained-release curve thereof was as shown in FIG. 2. It can be seen that the metformin hydrochloride osmotic pump tablet can reach the same drug controlled-release effect in the phosphate buffer solution of pH 6.8 at 50 r/min in the paddle method as that in the related technics.

Example 3

In this example, the used amount of other raw materials and preparation methods were the same as those in Example 1, except that the raw materials were used in the proportions as shown in Table 3, an ellipse-shaped punch of 19×15.8 mm was used, and the coating was stopped until the weight gain of the coating reached about 3%.

TABLE 3

Table of proportions of raw materials

| Components | | Gram/batch |
|---|---|---|
| Drug-containing granule | Metformin hydrochloride | 1000 |
| | Sodium lauryl sulfate | 15 |
| | Polysorbate | 155 |
| The binder solution | Povidone K30 | 10 |
| | 95% Ethanol | 90 |
| Added adjuvant materials | Magnesium stearate | 10 |
| Coating liquid | Cellulose acetate | 25 |
| | Polyethylene glycol 3350 | 15 |
| | Acetone | 710 |
| | Water | 40 |

The metformin hydrochloride osmotic pump tablet with a specification of 1000 mg prepared in this example had a tablet weight of only about 1.2 g, and a ratio of the long diameter to the short diameter of 1.2, and the cross-sectional area thereof can be reduced by 40-50% compared with that of the conventional sustained-release tablet (pressed by use of a circular-shaped punch), and it can reach the same drug controlled-release effect as that in the related technics.

Example 4

In this example, the used amount of other raw materials and preparation methods were the same as those in Example 1, except that the raw materials were used in the proportions as shown in Table 4, an ellipse-shaped punch of 19×4.75 mm was used, and the coating was stopped until the weight gain of the coating reached about 8%.

TABLE 4

Table of proportions of raw materials

| Components | | Gram/batch |
|---|---|---|
| Drug-containing granule | Metformin hydrochloride | 1000 |
| | Sodium lauryl sulfate | 40 |
| | Polysorbate | 150 |
| The binder solution | Povidone K30 | 13 |
| | 95% Ethanol | 87 |
| Added adjuvant materials | Magnesium stearate | 7 |
| Coating liquid | Cellulose acetate | 30 |
| | Polyethylene glycol 3350 | 10 |
| | Acetone | 715 |
| | Water | 40 |

The metformin hydrochloride osmotic pump tablet with a specification of 1000 mg prepared in this Example had a tablet weight of only about 1.2 g, and a ratio of the long diameter to the short diameter of 4, and the cross-sectional area thereof can be reduced by 40-50% compared with that of the conventional sustained-release tablet (pressed by use of a circular-shaped punch), and it can reach the same drug controlled-release effect as that in the related technics.

Example 5

In this example, the used amount of other raw materials and preparation methods were the same as those in Example 1, except that the raw materials were used in the proportions as shown in Table 5, an ellipse-shaped punch of 19×7.9 mm was used, and the coating was stopped until the weight gain of the coating reached about 2.5%.

TABLE 5

Table of proportions of raw materials

| Components | | Gram/batch |
|---|---|---|
| Drug-containing granule | Metformin hydrochloride | 1000 |
| | Sodium lauryl sulfate | 30 |
| | Mannitol | 100 |
| The binder solution | Hypromellose E3 | 10 |
| | Water | 290 |
| Added adjuvant materials | Magnesium stearate | 5 |
| Coating liquid | Ethyl cellulose | 20 |
| | Polyethylene glycol 3350 | 20 |
| | Absolute ethanol | 720 |
| | Water | 40 |

The metformin hydrochloride osmotic pump tablet with a specification of 1000 mg prepared in this example had a tablet weight of only about 1.2 g, and a ratio of the long diameter to the short diameter of 2.4, and the cross-sectional area thereof can be reduced by 40-50% compared with that of the conventional sustained-release tablet (pressed by use of a circular-shaped punch), and it can reach the same drug controlled-release effect as that in the related technics.

Example 6

In this example, the used amount of other raw materials and preparation methods were the same as those in Example 1, except that the raw materials were used in the proportions as shown in Table 6, an ellipse-shaped punch of 19×7.9 mm was used, and the coating was stopped until the weight gain of the coating reached about 10%.

TABLE 6

Table of proportions of raw materials

| | Components | Gram/batch |
|---|---|---|
| Drug-containing granule | Metformin hydrochloride | 1000 |
| | Sodium lauryl sulfate | 20 |
| | Mannitol | 100 |
| The binder solution | Hypromellose E3 | 17 |
| | Water | 287 |
| Added adjuvant materials | Magnesium stearate | 5 |
| Coating liquid | Ethyl cellulose | 20 |
| | Polyethylene glycol 3350 | 20 |
| | Absolute ethanol | 720 |
| | Water | 40 |

The metformin hydrochloride osmotic pump tablet with a specification of 1000 mg prepared in this example had a tablet weight of only about 1.2 g, and a ratio of the long diameter to the short diameter of 2.4, and the cross-sectional area thereof can be reduced by 40-50% compared with that of the conventional sustained-release tablet (pressed by use of a circular-shaped punch), and it can reach the same drug controlled-release effect as that in the related technics.

Example 7

In this example, the used amount of other raw materials and preparation methods were the same as those in Example 1, except that an ellipse-shaped punch of 19×10.6 mm was used.

The metformin hydrochloride osmotic pump tablet with a specification of 1000 mg prepared in this example had a tablet weight of only about 1.2 g, and a ratio of the long diameter to the short diameter of 1.8, and the cross-sectional area thereof can be reduced by 40-50% compared with that of the conventional sustained-release tablet (pressed by use of a circular-shaped punch), and it can reach the same drug controlled-release effect as that in the related technics.

Example 8

In this example, the used amount of other raw materials and preparation methods were the same as those in Example 1, except that an ellipse-shaped punch of 19×7 mm was used.

The metformin hydrochloride osmotic pump tablet with a specification of 1000 mg prepared in this example had a tablet weight of only about 1.2 g, and a ratio of the long diameter to the short diameter of 2.7, and the cross-sectional area thereof can be reduced by 40-50% compared with that of the conventional sustained-release tablet (pressed by use of a circular-shaped punch), and it can reach the same drug controlled-release effect as that in the related technics.

Example 9

In this example, the used amount of other raw materials and preparation methods were the same as those in Example 1, except that an ellipse-shaped punch of 19×6.3 mm was used.

The metformin hydrochloride osmotic pump tablet with a specification of 1000 mg prepared in this example had a tablet weight of only about 1.2 g, and a ratio of the long diameter to the short diameter of 3, and the cross-sectional area thereof can be reduced by 40-50% compared with that of the conventional sustained-release tablet (pressed by use of a circular-shaped punch), and it can reach the same drug controlled-release effect as that in the related technics.

Example 10

In this example, the used amount of other raw materials and preparation methods were the same as those in Example 1, except that an ellipse-shaped punch of 19×12.7 mm was used.

The metformin hydrochloride osmotic pump tablet with a specification of 1000 mg prepared in this example had a tablet weight of only about 1.2 g, and a ratio of the long diameter to the short diameter of 1.5, and the cross-sectional area thereof can be reduced by 40-50% compared with that of the conventional sustained-release tablet (pressed by use of a circular-shaped punch), and it can reach the same drug controlled-release effect as that in the related technics.

Example 11

In this example, the used amount of other raw materials and preparation methods were the same as those in Example 1, except that no drug release channels were produced on both sides of the tablet core after coating in step (6).

The metformin hydrochloride osmotic pump tablet with a specification of 1000 mg prepared in this example had a tablet weight of only about 1.2 g, and a ratio of the long diameter to the short diameter of 2.4, and the cross-sectional area thereof can be reduced by 50% compared with that of the conventional sustained-release tablet (pressed by use of a circular-shaped punch).

It can be seen from the comprehensive results of Example 1-11 that the preparation method of the present disclosure comprises: using a special-shaped punch-pressed metformin hydrochloride tablet core, and then wrapping the pressed metformin hydrochloride tablet core with a controlled-release coating film, such that a metformin hydrochloride osmotic pump tablet is prepared. The metformin hydrochloride osmotic pump tablet prepared by the present disclosure has a small tablet weight, and a metformin hydrochloride osmotic pump tablet with a specification of 1000 mg has a tablet weight of only about 1.2 g; on the premise that the obtained metformin hydrochloride osmotic pump tablet reaches the same drug controlled-release effect as that in the related technics, the cross-sectional area of the osmotic pump tablet is significantly reduced, which is reduced even more than 50%, compared to that of a circular-shaped tablet with the same weight, so that the resulting osmotic pump tablets are easier to be swallowed, greatly improving the compliance of patients.

Applicant has stated that although the detailed methods of the present disclosure have been described by the above examples, the present disclosure is not limited thereto, that is to say, it is not meant that the present disclosure has to be implemented depending on the above detailed methods. It will be apparent to those skilled in the art that any improvements made to the present disclosure, equivalent replacements and addition of adjuvant ingredients to the raw materials of the products of the present disclosure, and selections of the specific implementations, etc., all fall within the protection scope and the disclosed scope of the present disclosure.

The invention claimed is:

1. A preparation method of a metformin hydrochloride osmotic pump tablet, wherein the preparation method comprises: using a special-shaped punch to press a metformin hydrochloride tablet core, and wrapping the pressed metformin hydrochloride tablet core with a controlled-release coating film to prepare a metformin hydrochloride osmotic pump tablet,
wherein the special-shaped punch is a capsule-shaped punch or an ellipse-shaped punch; when a special-shaped punch is used, a ratio of a long diameter to a short diameter of the metformin hydrochloride tablet core is controlled to be from 1.2 to 4,
wherein the method comprises the following steps:
(1) formulating a binder solution, mixing the metformin hydrochloride, a tablet core adjuvant material and the binder solution for granulation, and then drying and granulating;
(2) pressing granules obtained by the granulation via a special-shaped punch into a metformin hydrochloride tablet core;
(3) wrapping the prepared metformin hydrochloride tablet core with a controlled-release coating film to obtain a metformin hydrochloride osmotic pump tablet,
wherein the tablet core adjuvant material in step (1) comprises sodium lauryl sulfate and a filler; wherein the filler is any one or a combination of at least two of polysorbate, sorbitol or mannitol, and
wherein in step (1), the binder solution, metformin hydrochloride, sodium lauryl sulfate and the filler are mixed in the following parts by weight:

| metformin hydrochloride | 1000 parts |
| sodium lauryl sulfate | 5-70 parts |
| filler | 100-155 parts |
| the binder solution | 95-300 parts. |

2. The preparation method according to claim 1, wherein a drug release channel is produced on the controlled-release coating film wrapping the metformin hydrochloride osmotic pump tablet;
wherein the number of the drug release channel is 1 or more.

3. The preparation method according to claim 1, wherein after the metformin hydrochloride tablet core is wrapped with a controlled-release coating film, the weight gain of the controlled-release coating film is 2 wt % or more.

4. The preparation method according to claim 1, wherein formulating a binder solution in step (1) is performed by way of mixing a binder with a solvent to prepare a binder solution;
wherein the binder is any one or a combination of at least two of povidone, hypromellose or hydroxypropylcellulose;
wherein the solvent is ethanol having a purity of 95 wt % and/or water.

5. The preparation method according to claim 4, wherein when the binder is povidone and the solvent is ethanol having a purity of 95 wt %, the mass ratio of povidone to ethanol having a purity of 95 wt % is (10-15):(90-85);
alternatively, wherein when the binder is hypromellose and the solvent is water, the mass ratio of hypromellose to water is (10-15):(290-285).

6. The preparation method according to claim 1, wherein in step (1), the binder solution, metformin hydrochloride, sodium lauryl sulfate and polysorbate are mixed in the following parts by weight:

| metformin hydrochloride | 1000 parts |
| sodium lauryl sulfate | 5 parts |
| polysorbate | 150 parts |
| the binder solution | 100 parts. |

7. The preparation method according to claim 1, wherein in the step (1), the binder solution, metformin hydrochloride, sodium lauryl sulfate and mannitol are mixed in the following parts by weight:

| metformin hydrochloride | 1000 parts |
| sodium lauryl sulfate | 25 parts |
| mannitol | 100 parts |
| the binder solution | 300 parts. |

8. The preparation method according to claim 1, wherein a lubricant is added to the granulation process in step (1).

9. The preparation method according to 8, the lubricant is magnesium stearate;
wherein the lubricant is added in an amount from 0.5% to 1% of the mass of metformin hydrochloride.

10. The preparation method according to claim 1, wherein the coating liquid used in the process of wrapping with the controlled-release coating film comprises a controlled-release material and a porogen.

11. The preparation method according to 10, wherein the controlled-release material is cellulose acetate and/or ethyl cellulose;
wherein the porogen is polyethylene glycol.

12. The preparation method according to 10, wherein the coating liquid is mainly composed of the following components in parts by weight:

| the controlled-release material | 20-30 parts |
| porogen | 10-20 parts |
| solvent | 750-760 parts. |

13. The preparation method according to 12, wherein the solvent is any one or a combination of at least two of ethanol, acetone or water.

14. A metformin hydrochloride osmotic pump tablet prepared by the preparation method according to claim 1, comprising a metformin hydrochloride tablet core and a controlled-release coating film wrapping the metformin hydrochloride tablet core, wherein the ratio of the long diameter to the short diameter of the metformin hydrochloride osmotic pump tablet is from 1.2 to 4.

15. The metformin hydrochloride osmotic pump tablet according to claim 14, wherein the metformin hydrochloride osmotic pump tablet is non-circular-shaped.

16. The metformin hydrochloride osmotic pump tablet according to claim 15, the metformin hydrochloride osmotic pump tablet is capsule-shaped or ellipse-shaped.

* * * * *